(12) United States Patent
Satou et al.

(10) Patent No.: US 7,896,820 B2
(45) Date of Patent: Mar. 1, 2011

(54) GUIDE WIRE

(75) Inventors: Hideo Satou, Fujinomiya (JP); Hideki Fujimagari, Fujinomiya (JP); Fumihiko Mouri, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/004,414

(22) Filed: Dec. 21, 2007

(65) Prior Publication Data

US 2008/0154152 A1   Jun. 26, 2008

Related U.S. Application Data

(60) Provisional application No. 60/877,407, filed on Dec. 28, 2006.

(30) Foreign Application Priority Data

Dec. 26, 2006   (JP) .............................. 2006-350692

(51) Int. Cl.
 *A61B 5/00* (2006.01)
 *A61M 25/00* (2006.01)
(52) U.S. Cl. ..................................... 600/585
(58) Field of Classification Search .................. 600/585
 See application file for complete search history.

(56) References Cited

U.S. PATENT DOCUMENTS

| | | | |
|---|---|---|---|
| 4,925,445 A | 5/1990 | Sakamoto et al. | |
| 5,069,226 A | 12/1991 | Yamauchi et al. | |
| 5,238,004 A | 8/1993 | Sahatjian et al. | |
| 5,269,759 A | 12/1993 | Hernandez et al. | |
| 5,341,817 A * | 8/1994 | Viera | 600/585 |
| 5,354,623 A | 10/1994 | Hall | |
| 5,368,049 A | 11/1994 | Raman et al. | |
| 5,402,799 A | 4/1995 | Colon et al. | |
| 5,411,476 A | 5/1995 | Abrams et al. | |
| 5,452,726 A | 9/1995 | Burmeister et al. | |
| 5,497,786 A | 3/1996 | Urick | |
| 5,498,250 A | 3/1996 | Prather | |

(Continued)

FOREIGN PATENT DOCUMENTS

JP    1-124473 A    5/1989

(Continued)

*Primary Examiner*—Max Hindenburg
*Assistant Examiner*—Sean P Dougherty
(74) *Attorney, Agent, or Firm*—Buchanan Ingersoll & Rooney PC

(57) ABSTRACT

A guide wire includes a first wire disposed on the distal side and composed of a first material, and a second wire disposed on the proximal side of the first wire and composed of a second material. The first and second wires are connected to each other through an intermediate member which includes a core portion and an outer layer covering the outer periphery of the core portion. The core portion is wholly or partly composed of a material different from the material of the outer layer, and at least one of the core portion and the outer layer is composed of the first material or the second material. The proximal portion of the first wire and the distal portion of the intermediate member are joined to each other, and the distal portion of the second wire and the proximal portion of the intermediate member are joined to each other.

26 Claims, 5 Drawing Sheets

U.S. PATENT DOCUMENTS

| | | |
|---|---|---|
| 5,695,111 A | 12/1997 | Nanis et al. |
| 5,772,609 A | 6/1998 | Nguyen et al. |
| 5,797,857 A | 8/1998 | Obitsu |
| 5,876,356 A | 3/1999 | Viera et al. |
| 5,916,177 A * | 6/1999 | Schwager .................. 600/585 |
| 5,924,998 A | 7/1999 | Cornelius et al. |
| 5,951,494 A | 9/1999 | Wang et al. |
| 6,001,068 A | 12/1999 | Uchino et al. |
| RE36,628 E | 3/2000 | Sagae et al. |
| 6,093,157 A | 7/2000 | Chandrasekaran |
| 6,165,292 A | 12/2000 | Abrams et al. |
| 6,183,424 B1 * | 2/2001 | Schwager .................. 600/585 |
| 6,234,981 B1 | 5/2001 | Howland |
| 6,390,992 B1 | 5/2002 | Morris et al. |
| 6,520,923 B1 | 2/2003 | Jalisi |
| 6,544,197 B2 * | 4/2003 | DeMello .................... 600/585 |
| 6,602,208 B2 | 8/2003 | Jafari |
| 6,679,853 B1 | 1/2004 | Jalisi |
| 6,702,762 B2 | 3/2004 | Jafari et al. |
| 2003/0069521 A1 * | 4/2003 | Reynolds et al. ............ 600/585 |
| 2004/0030266 A1 | 2/2004 | Murayama et al. |
| 2004/0039308 A1 | 2/2004 | Murayama et al. |
| 2004/0039309 A1 | 2/2004 | Murayama et al. |
| 2004/0064069 A1 * | 4/2004 | Reynolds et al. ............ 600/585 |
| 2004/0193073 A1 * | 9/2004 | DeMello et al. ............. 600/585 |
| 2005/0152731 A1 | 7/2005 | Mishima et al. |

FOREIGN PATENT DOCUMENTS

| | | |
|---|---|---|
| JP | 2004/230140 A | 8/2004 |

\* cited by examiner

GUIDE WIRE

This application claims priority under 35 U.S.C. §119(e) to U.S. Provisional Application No. 60/877,407 filed on Dec. 28, 2006, the entire content of which is incorporated herein by reference. This application is also based on and claims priority to Japanese Application No. 2006-350692 filed on Dec. 26, 2006, the entire content of which is incorporated herein.

TECHNOLOGICAL FIELD

The present invention generally relates to a guide wire. More specifically, the invention pertains to a guide wire used in guiding a catheter into a body lumen such as a blood vessel and a bile duct.

BACKGROUND DISCUSSION

Guide wires are used to guide a catheter in treating sites at which open surgery is difficult or which require minimal invasiveness to the body, for example, PTCA (Percutaneous Transluminal Coronary Angioplasty), or in examination such as angiocardiography. A guide wire used in the PTCA procedure is inserted, with the distal end projecting from the distal end of a balloon catheter, into the vicinity of a target angiostenosis portion together with the balloon catheter, and is operated to guide the distal portion of the balloon catheter to the target angiostenosis portion.

In PTA (Percutaneous Transluminal Angioplasty) also, for opening a stenosis portion (occluded portion) in a peripheral blood vessel such as femoral, iliac, renal and shunt blood vessels, a distal portion of a balloon catheter is guided to the vicinity of an angiostenosis portion by use of a guide wire, like in the PTCA procedure.

Since the blood vessels to which such a treating method is applied are bent in a complicated manner, a guide wire used to insert a balloon catheter into the blood vessel is required to have, for example, appropriate flexibility and resilience against bending, pushability and torque transmission performance (generically called "steerability") for transmitting an operational force from the proximal portion to the distal side, and further, kink resistance (resistance against sharp bending) and the like.

Guide wires intended to provide steerability and flexibility at the distal portion of the guide wire include guide wires formed from different materials, particularly guide wires having a first wire composed of an Ni—Ti alloy and a second wire composed of stainless steel.

In the above guide wire, the first wire composed of an Ni—Ti alloy and the second wire composed of stainless steel are joined by butt resistance welding, whereby the first and second wires can be joined comparatively firmly, as contrasted to other welding methods where a brittle Fe—Ti based intermetallic compound would be produced with the result of insufficient joint strength.

In addition, the weld portion is provided with a projected portion projected in the outer circumferential direction (radially outward direction) so that the joint strength is enhanced by the projected portion and the stress generated when the guide wire is bent is dispersed.

SUMMARY

According to one aspect, a guide wire includes a first wire disposed on the distal side and composed of a first material, and a second wire disposed on the proximal side of the first wire and composed of a second material. The first and second wires are connected to each other through an intermediate member to constitute a wire body. The intermediate member has a core portion, and an outer layer covering the outer periphery of the core portion. The core portion is wholly or partly composed of a material different from the material of the outer layer, and at least one of the core portion and the outer layer is composed of the first material or the second material. A proximal portion of the first wire and a distal portion of the intermediate member are joined to each other, and a distal portion of the second wire and a proximal portion of the intermediate member are joined to each other.

The first material preferably is a Ni—Ti alloy. The second material can be a stainless steel. A proximal portion of the first wire preferably is lower than the intermediate member in rigidity. A distal portion of the second wire can be higher than the intermediate member in rigidity. The outside diameter of the wire body can be substantially constant along the longitudinal direction of the wire body at least at a portion of the wire body, ranging from a proximal portion of the first wire to a distal portion of the second wire. The core portion is preferably composed of one of the first and second materials, and the outer layer is preferably composed of the other of the first material and the second material. The core portion is preferably composed of one of a Ni alloy and the second material, while the outer layer is preferably composed of the other of a Ni alloy and the second material.

The core portion can be composed of a distal-side member disposed on the distal side, and a proximal-side member disposed on the proximal side of the distal-side member and composed of a material different from the material of the distal-side member. The distal-side member preferably is composed of the first material, and the proximal-side member is composed of the second material. The outer layer is preferably composed of the first material or the second material. The outer layer preferably is composed of a Ni alloy or a Co alloy. A proximal end face of the first wire and a distal end face of the intermediate member preferably are joined to each other, and a distal end face of the second wire and a proximal end face of the intermediate member are joined to each other.

In one version, the outer layer has an extension portion extending distally beyond the distal end of the core portion, with the extension portion covering the outer periphery of the proximal portion of the first wire.

The core portion can be composed of the second material. The outer layer can be composed of the first material. The outer layer preferably is composed of a Ni alloy. The outer peripheral surface of the proximal portion of the first wire and the inner peripheral surface of the outer layer of the intermediate member are preferably joined to each other, and a distal end face of the second wire and a proximal end face of the intermediate member are joined to each other.

Alternatively, the outer layer can include an extension portion extending proximally beyond the proximal end of the core portion. The extension portion may cover the outer periphery of a distal portion of the second wire.

The proximal end face of the first wire and the distal end face of the intermediate member are preferably joined to each other, and the outer peripheral surface of the distal portion of the second wire and the inner peripheral surface of the outer layer of the intermediate member are joined to each other. The core portion and the outer layer of the intermediate member can be crimped to each other. The intermediate member preferably is substantially cylindrical or substantially frustoconical in shape. The proximal portion of the first wire and the distal portion of the intermediate member may be joined to each other by welding, soldering or brazing, and the distal portion of the second wire and the proximal portion of the intermediate member are joined to each other by welding, soldering or brazing.

According to another aspect, a guide wire comprises a first wire made of a first material, a second wire made of a second material different from the first material, wherein the first wire is positioned at a distal portion of the guide wire, and wherein the second wire is positioned proximally of the first wire. An intermediate member is positioned between the first wire and the second wire, and the intermediate member comprises a core portion and an outer layer, with the outer layer covering the outer periphery of the core portion. The core portion is at least in part made of a material different from material of which the outer layer is made, and at least one of the core portion and the outer layer is made of the first material or the second material. The core portion possesses a distal end and a proximal end, and the first wire possesses a proximal portion joined to the distal portion of the intermediate member. A portion of the first wire located distally of the proximal portion of the first wire possesses an outer diameter that decreases in the distal direction, and the second wire possesses a distal portion joined to the proximal portion of the intermediate member. The outer diameter of the intermediate member and the outer diameter of the first wire are the same in a first transition region at which the outer layer of the intermediate member transitions to the first wire, and the outer diameter of the intermediate member and the outer diameter of the second wire are the same in a second transition region at which the outer layer of the intermediate member transitions to the second wire.

BRIEF DESCRIPTION OF THE DRAWING FIGURES

The foregoing and additional features and aspects of the guide wire will become more apparent from the following detailed description considered with reference to the accompanying drawing figures briefly described below.

DETAILED DESCRIPTION

Figure 1:
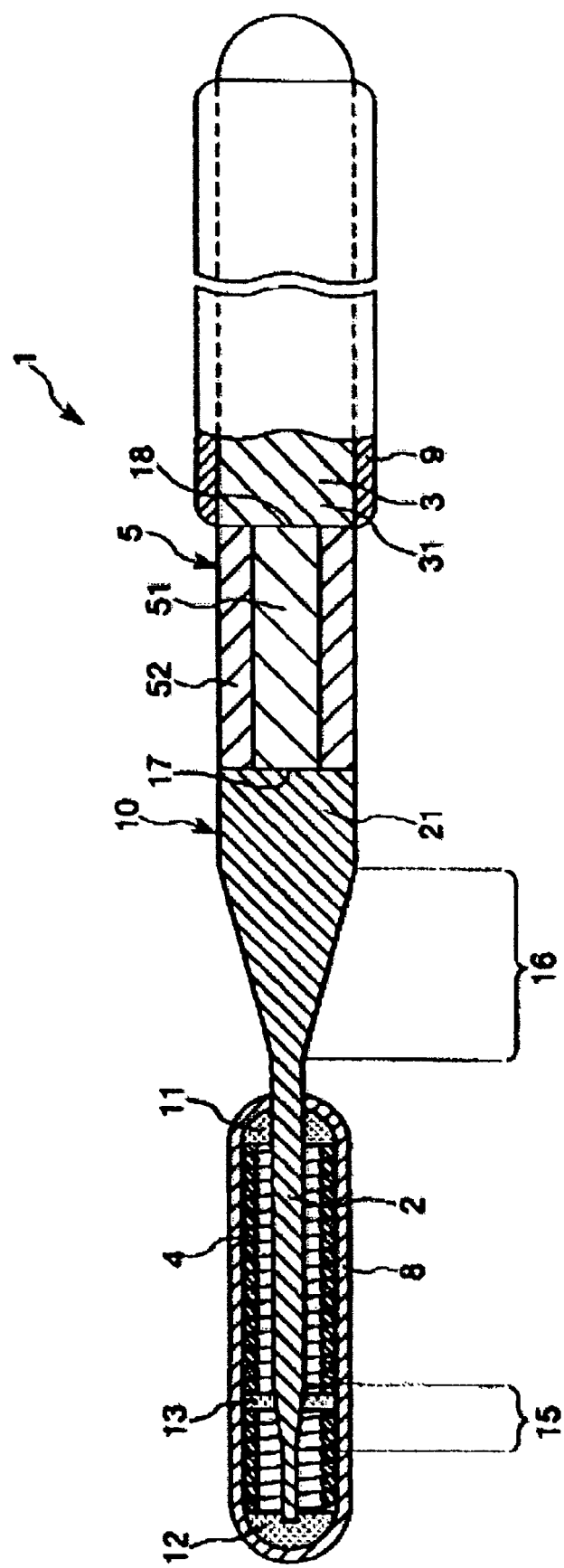
FIG. 1 is a longitudinal cross-sectional view of a first embodiment of the guide wire disclosed here.

FIG. 1 illustrates, in longitudinal cross-sectional view, one embodiment of the guide wire disclosed herein. The right side in FIG. 1 is referred to as the "proximal" end, and the left side in FIG. 1 is referred to as the "distal" end. In addition, in FIG. 1, for ease in understanding, the guide wire is schematically shown in the state of being shortened in the longitudinal direction and exaggerated in the radial (diametrical) direction relative to the actual dimensions of the guide wire. Thus, the ratio between the dimensions in the longitudinal direction and in the radial direction is different from the actual or practical ratio.

The guide wire 1 shown in FIG. 1 is a catheter guide wire having useful application for being inserted in the lumen of a catheter (inclusive of endoscope). The guide wire 1 includes a wire body 10 in which a first wire 2 disposed on the distal side and a second wire 3 disposed on the proximal side of the first wire 2 are connected to each other through an intermediate member 5. The guide wire 1 also includes a spiral coil 4. The overall length of the guide wire 1 is preferably about 200 to 5000 mm. In addition, the outer diameter of the guide wire 1 is preferably about 0.2 to 1.2 mm.

The first wire 2 is composed of a flexible or elastic filamentous member. The length of the first wire 2 is not particularly limited, and is preferably about 20 to 1000 mm.

In this embodiment, the first wire 2 has a portion having a constant outer diameter, and a tapered portion (gradually reduced outer diameter portion) in which the outer diameter is gradually reduced along the distal direction. The latter portion may be provided at one location or at two or more locations. In the embodiment shown in FIG. 1, two gradually reduced outer diameter portions 15, 16 are provided.

By virtue of the gradually reduced outer diameter portions 15, 16, the rigidity (flexural rigidity, torsional rigidity) of the first wire 2 is gradually reduced in the distal direction. As a result, the guide wire 1 exhibits good flexibility at its distal portion, whereby trackability in relation to a blood vessel or the like and safety are enhanced, and sharp bending (kinking) and the like can be prevented.

The taper angle (outer diameter reduction rate) of each of the gradually reduced outer diameter portions 15, 16 may be constant along the longitudinal direction of the wire body 10 (hereinafter referred to simply as "the longitudinal direction") or may vary along the longitudinal direction in some location. For example, the gradually reduced outer diameter portion may be so formed that portions with a comparatively larger taper angle (outer diameter reduction rate) and portions with a comparatively smaller taper angle are alternately repeated a plurality of times.

The proximal-side portion (the portion on the proximal side relative to the gradually reduced outer diameter portion 16) of the first wire 2 is constant in outer diameter to the proximal end of the first wire 2.

In the embodiment shown in FIG. 1, the distal-side portion (the portion on the distal side of the gradually reduced outer diameter portion 15) of the first wire 2 is constant in outer diameter to the distal-most end of the first wire 2.

The material from which is fabricated the first wire 2 (the blank material of the first wire 2 or the first material) is not particularly limited, and various metallic materials such as Ni—Ti alloys and stainless steels can be used. Preferred materials are alloys exhibiting pseudoelasticity (inclusive of superelastic alloys). More preferably, superelastic alloys are used. A superelastic alloy is comparatively flexible, has resilience and is less liable to acquire a tendency toward a certain bending. Therefore, with the first wire 2 composed of a superelastic alloy, the guide wire 1 can have sufficient flexibility and resilience against bending at its distal-side portion, so that trackability in relation to complicatedly curved or bent blood vessels is enhanced, and more excellent steerability can be obtained. In addition, the resilience of the first wire 2 prevents the first wire 2 from acquiring a tendency toward a certain bending (i.e., a set) even when the first wire 2 is repeatedly curved or bent, so that it is possible to prevent the steerability from being lowered due to a tendency toward a certain bending which might otherwise be acquired by the first wire 2 during use of the guide wire 1.

Possible elastic (superelastic) metals which can be utilized include those elastic metals whose stress-distortion curve by tension has a variety of shapes, and also those elastic metals whose transformation temperature can or cannot be measured such as As (austenite start temperature), Af (austenite finish temperature), Ms (martensite start temperature), and Mf (martensite finish temperature). Further, all of those superelastic metals which are deformed (distorted) by a relatively great amount by stress and return to their original shape in response to removal of the stress are included. Thus, superelastic alloys includes those which exhibit different tensile stress vs. strain curves (i.e., the superelastic alloys which can be used here are not limited to superelastic alloys having a particular tensile stress vs. strain curve), those which have transformation points such as As, Af, Ms, Mf, whether they are clearly measurable or not, and those which are largely deformed (strained) under stresses and return to their original shape upon removal of the stresses.

As a preferred composition of the superelastic alloy, Ni—Ti-based alloys such as a Ni—Ti alloy containing Ni by 49 to 52 atom %, a Cu—Zn alloy containing Zn by 38.5 to 41.5 weight %, Cu—Zn—X alloys (X is at least one of Be, Si, Sn, Al, and Ga) containing X by 1 to 10 weight %, a Ni—Al alloy containing Al by 36 to 38 atom %, and so forth may be used. Among these, the Ni—Ti-based alloys described above are particularly preferable. It is to be noted that the superelastic alloy represented by Ni—Ti-based alloys is excellent also in adhesive property of a coating layer 5 hereinafter described.

The second wire 3 is disposed on the proximal side of the intermediate member 5 which will be described later. The second wire 3 is composed of a flexible or elastic filamentous member. The length of the second wire 3 is not particularly limited, and is preferably about 20 to 4800 mm.

In the version of the guide wire shown in FIG. 1, the outer diameter of the second wire 3 is constant (inclusive of substantially constant) along its entire longitudinal extent, and is equal (inclusive of approximately equal) to the outer diameter of the proximal end of the first wire 2.

The second wire 3 is composed of a material different from the material of the first wire 2. Particularly, the second wire 3 is preferably composed of a material higher in elasticity (Young's modulus (modulus of longitudinal elasticity), modulus of rigidity (modulus of transverse elasticity), bulk modulus) than the material constituting the first wire 2. This helps ensure that the second wire 3 possesses appropriate rigidity (flexural rigidity, torsional rigidity), that the guide wire 1 is relatively high in the so-called flexural strength, that the pushability and torque transmission performance of the guide wire 1 are enhanced, and that better insertion steerability of the guide wire can be obtained.

The material forming the second wire 3 (the blank material of the second wire 3), or the second material, is not particularly limited insofar as it is different from the material constituting the first wire 2, and various metallic materials such as stainless steels (for example, all SUS steels such as SUS304, SUS303, SUS316, SUS316L, SUS316J1, SUS316J1L, SUS405, SUS430, SUS434, SUS444, SUS429, SUS430F, and SUS302), piano wire, cobalt alloys, and pseudoelastic alloys. Among these metallic materials, preferred are stainless steels and cobalt alloys, and more preferred are stainless steels. When the second wire 3 is composed of a stainless steel or a cobalt alloy, the guide wire 1 can have more excellent pushability and torque transmission performance.

The intermediate member 5 is disposed between the first wire 2 and the second wire 3. The end portions of the first wire 2 and the intermediate member 5 are joined to each other, and the end portions of the second wire 3 and the intermediate member 5 are joined to each other. Specifically, end faces of the first wire 2 and the intermediate member 5 are connected to each other, and the end faces of the second wire 3 and the intermediate member 5 are connected to each other.

The proximal portion 21 of the first wire 2 and the distal portion of the intermediate member 5 are joined to each other, and the distal portion 31 of the second wire 3 and the proximal portion of the intermediate member 5 are joined to each other.

More specifically, the proximal end face of the proximal portion 21 of the first wire 2 and the distal end face of the distal portion of the intermediate member 5 are joined to one another, and the distal end face of the distal portion 31 of the second wire 3 and the proximal face of the proximal portion of the intermediate member 5 are joined to one another.

The intermediate member 5 is composed of a flexible or elastic filamentous material, preferably as a filamentous member. In the illustrated embodiment shown in FIG. 1, the intermediate member 5 is substantially cylindrical in shape, and its outer diameter is equal (inclusive of approximately equal) to the outer diameter of the proximal end of the first wire 2 and the outer diameter of the distal end of the second wire 3. Specifically, the outer diameter of the wire body 10 is constant (inclusive of substantially constant) along the longitudinal direction at a portion, ranging from the proximal portion 21 of the first wire 2 to the proximal portion of the second wire 3 (ranging at least from the proximal portion 21 of the first wire 2 to the distal portion 31 of the second wire 3), of the wire body 10. In other words, the outer peripheral surface of the wire body 10 constitutes a continuous surface substantially free of steps. This helps ensure that the guide wire 1 is not likely to be caught in the body during use, and so the guide wire 1 is relatively easy to operate (steer), and safety is enhanced.

The intermediate member 5 is composed of a core portion 51 and an outer layer 52 covering the outer periphery of the core portion 51. In the illustrated version shown in FIG. 1, the core portion 51 is substantially cylindrical (columnar) in shape, and the outer layer 52 has a tubular shape with a substantially circular cross-sectional shape. In the illustrated embodiment, the outer diameter of the core portion 51 is constant throughout its length.

The core portion 51 and the outer layer 52 are fixed to each other, for example by crimping. The method for fixing the core portion 51 and the outer layer 52 to each other is not limited to crimping, and other methods may also be used. However, crimping is preferable from the viewpoint of making it possible to fix them to each other relatively easily and firmly.

The core portion 51 (the entirety of the core portion 51) is composed of a material different from the material of the outer layer 52, and at least one of the core portion 51 and the outer layer 52 is composed of the first material (the same material as the material of the first wire 2) or the second material (the same material as the material of the second wire 3).

In this embodiment, the following four configurations (1) to (4) are preferable.

[Configuration 1]

The core portion 51 is composed of the second material, and the outer layer 52 is composed of the first material.

This construction in which the material constituting the first wire 2 and the material constituting the outer layer 52 are the same helps ensure that the proximal end face of the first wire 2 and the distal end face of the outer layer 52 are joined particularly firmly. In addition, with the material constituting the second wire 3 and the material constituting the core portion 51 being the same, the distal end face of the second wire 3 and the proximal end face of the core portion 51 are also joined particularly firmly. As a result, the first wire 2 and the second wire 3 are firmly connected to each other through the intermediate member 5.

[Configuration 2]

The core portion 51 is composed of the first material, and the outer layer 52 is composed of the second material.

With this construction in which the material constituting the first wire 2 and the material constituting the core portion 51 are the same, the proximal end face of the first wire 2 and the distal end face of the core portion 51 are joined particularly firmly. In addition, with the material constituting the second wire 3 and the material constituting the outer layer 52 being the same, the distal end face of the second wire 3 and the proximal end face of the outer layer 52 are joined particularly firmly. As a result, the first wire 2 and the second wire 3 are firmly connected to each other through the intermediate member 5.

[Configuration 3]

The core portion 51 is composed of the second material, and the outer layer 52 is composed of a Ni alloy. Ni alloys which may be used in this regard include any alloy that contains Ni as a constituent element. Examples of the Ni alloy include Ni—Ti alloys, Ni—Cr alloys, Ni—Cu alloys, Co—Ni alloys, and Ni—Mn alloys.

Among these Ni alloys, preferred Ni alloys are those which contain Ni as a main constituent (Ni alloys composed mainly of Ni), i.e., Ni-based alloys (those alloys in which the content, by weight, of Ni is the highest of the contents of elements constituting the alloy).

In this configuration, especially in the case where a Ni—Ti alloy is used as the first constituent material, the proximal end face of the first wire 2 and the distal end face of the outer layer 52 are joined particularly firmly. In addition, the material constituting the second wire 3 and the material constituting the core portion 51 are the same, so that the distal end face of the second wire 3 and the proximal end face of the core portion 51 are joined particularly firmly. As a result, the first wire 2 and the second wire 3 are firmly connected to each other through the intermediate member 5.

[Configuration 4]

The core portion 51 is composed of a Ni alloy, and the outer layer 52 is composed of the second material.

This helps ensure that, especially in the case where a Ni—Ti alloy is used as the first constituent material, the proximal end face of the first wire 2 and the distal end face of the core portion 51 are joined particularly firmly. In addition, the material constituting the second wire 3 and the material constituting the outer layer 52 are the same, and so the distal end face of the second wire 3 and the proximal end face of the second wire 3 are joined particularly firmly. As a result, the first wire 2 and the second wire 3 are firmly connected to each other through the intermediate member 5. In this configuration, the Ni alloy forming the core portion 51 can be the same Ni alloys described above (in Configuration 3).

The rigidity (flexural rigidity, torsional rigidity) of the intermediate member 5 is between that of the proximal portion 21 of the first wire 2 and that of the distal portion 31 of the second wire 3. More specifically, the proximal portion 21 of the first wire 2 is lower in rigidity than the intermediate member 5, and the distal portion 31 of the second wire 3 is higher in rigidity than the intermediate member 5. This helps ensure that the wire body 10 of the guide wire 1 is gradually lowered in rigidity (flexural rigidity, torsional rigidity) along the distal direction from the intermediate portion in the longitudinal direction (axial direction) thereof. As a result, kink resistance (resistance against sharp bending) is enhanced, and the guide wire 1 possesses excellent steerability characteristics.

The rigidity of the intermediate member 5 remains constant irrespectively of the direction in which the intermediate member 5 is bent (irrespectively of the radially outward direction), whereby excellent steerability is obtained.

The method for joining the proximal portion 21 of the first wire 2 and the distal portion of the intermediate member 5 to each other and the method for joining the distal portion 31 of the second wire 3 and the proximal portion of the intermediate member 5 are not particularly limited, and various methods can be used for this purpose. However, a preferred joining method is welding.

As a result, a joint portion 17 between the proximal portion 21 of the first wire 2 and the distal portion of the intermediate member 5, and a joint portion 18 between the distal portion 31 of the second wire 3 and the proximal portion of the intermediate member 5 are provided with a high joint strength by a relatively simple method. Accordingly, in the guide wire 1, the torsional torque and pushing force from the second wire 3 are securely transmitted to the first wire 2.

The method of welding is not particularly limited. Examples of welding methods which can be used include friction welding, laser welding, butt resistance welding such as upset welding, and the like. Among these various welding methods, a particularly preferred method is butt resistance welding as this makes it possible to achieve a relatively high joint strength comparatively easily.

The length (the length in the longitudinal direction) of the intermediate member 5 is preferably about 5 to 150 mm, more preferably about 5 to 40 mm.

The outer diameter of the core portion 51 of the intermediate member 5 is preferably about 0.15 to 1.19 mm, more preferably about 0.17 to 1.15 mm.

The inner diameter of the outer layer 52, being approximately equal to the outer diameter of the core portion 51, is preferably about 0.15 to 1.19 mm, more preferably about 0.17 to 1.15 mm. The outer diameter of the outer layer 52 is preferably about 0.2 to 1.2 mm. The thickness of the outer layer 52 is preferably about 0.01 to 0.2 mm, more preferably about 0.01 to 0.05 mm.

The coil 4 is disposed at the outer periphery of the distal portion of the first wire 2. The coil 4 is a member obtained by spirally winding a filamentous material (thin wire), and is disposed to cover at least a distal-side portion of the first wire 2. In the illustrated embodiment of FIG. 1, the distal-side portion of the first wire 2 is positioned centrally inside of the coil 4. The distal-side portion of the first wire 2 is spaced from and outer of contact with the inside surface of the coil 4. The joint portion 17 between the proximal portion 21 of the first wire 2 and the distal portion of the intermediate member 5 is located on the proximal side relative to the proximal end of the coil 4.

In this embodiment, a slight gap exists between the adjacent turns of the spirally wound filamentous material when no external force is exerted on the coil. However, a configuration may be adopted in which the filamentous material is closely wound so that no gap exists between the adjacent turns when no external force is exerted.

The coil 4 is preferably composed of a metallic material. Examples of the metallic material constituting the coil 4 include stainless steels, superelastic alloys, cobalt alloys, noble metals such as gold, platinum, tungsten, etc. and alloys thereof (for example, platinum-iridium alloys). Particularly in the case where the coil 4 is composed of a radiopaque material such as noble metals, the guide wire 1 can be suited to radiography, and can be inserted into the body while confirming the position of the distal portion thereof under fluoroscopic observation, which is preferable. In addition, the coil 4 may be composed of different materials, on the distal side and on the proximal side thereof. For example, the coil 4 may be composed of a coil of a radiopaque material on the distal side, and a coil of comparatively radiolucent material (stainless steel or the like) on the proximal side. The overall length of the coil 4 is preferably about 5 to 500 mm.

The proximal portion and the distal portion of the coil 4 are fixed to the first wire 2 by fixing materials 11, 12, respectively. In addition, an intermediate portion (at a position nearer to the distal end) of the coil 4 is fixed to the first wire 2 by a fixing material 13. The fixing materials 11, 12, 13 are each composed of a solder or a brazing filler metal. The fixing materials 11, 12, 13 are not limited to a solder, and may each be an adhesive. The method for fixing the coil 4 is not limited to use of a fixing material as described. For example, the fixing may be carried out by welding. In addition, to prevent damage to the inside wall of a body lumen such as a blood vessel, the distal surface of the fixing material 12 is preferably rounded in shape.

In this embodiment, since the coil 4 is provided, the first wire 2 covered with the coil 4 has a small area of contact with a lumen in which it is passed, so that sliding resistance thereof can be reduced, and the steerability of the guide wire 1 is enhanced.

While the coil 4 is formed from a filamentous material having a circular cross-sectional shape in this embodiment, the coil is not limited in this regard. The filamentous material may have, for example, an elliptical cross-sectional shape, a tetragonal (especially rectangular) cross-sectional shape or other cross-sectional shapes.

The wire body 10 is provided with a resin coating layer(s) covering the entire outer peripheral surface or a part of the outer peripheral surface (outside surface). In the embodiment shown in FIG. 1, axially spaced apart resin coating layers 8, 9 are provided on the outer periphery of the first wire 2 and the second wire 3 respectively.

The resin coating layers 8, 9 can be formed for various purposes. An example is to reduce the friction (sliding resistance) of the guide wire 1 and to enhance the slidability of the guide wire 1, thereby enhancing the steerability of the guide wire 1.

In a variation on the embodiment shown in FIG. 1, the resin coating layer 8 or 9 may be provided to cover the outer periphery of the gradually reduced outer diameter portion 16. This makes it possible to further moderate the variation in outer diameter (variation in taper angle, or the like) of the wire body 10, to further enhance the pushability, torque transmission performance and kink resistance of the guide wire 1, and to enhance steerability for moving in the longitudinal direction of the guide wire 1.

To achieve a reduction in the friction (sliding resistance) of the guide wire 1, the resin coating layers 8, 9 are preferably composed of a friction reducing material as will be described below. This helps ensure that the frictional resistance (sliding resistance) between the guide wire 1 and the inside wall of a catheter used together with the guide wire 1 is reduced, slidability of the guide wire 1 is enhanced, and the steerability of the guide wire 1 in the catheter is enhanced. In addition, since the sliding resistance of the guide wire 1 is lowered, it is possible, when the guide wire 1 is moved and/or rotated in a catheter, to relatively reliably inhibit or prevent kinking (sharp bending) or torsion of the guide wire 1, particularly, kinking or torsion in the vicinity of the joint portions 17, 18.

Examples of the material for the layers 8, 9 which can reduce friction include polyolefins such as polyethylene, polypropylene, etc., polyvinyl chloride, polyesters (PET, PBT, etc.), polyamides, polyimides, polyurethane, polystyrene, polycarbonates, silicone resins, fluororesins (PTFE, ETFE, etc.), and composite materials thereof.

Among these materials, fluororesins (or composite materials thereof can be favorably used, wherein the frictional resistance (sliding resistance) between the guide wire 1 and the inside wall of a catheter is reduced more effectively, the slidability of the guide wire 1 is enhanced, and the steerability of the guide wire 1 in the catheter is improved. In addition, this makes it possible, when the guide wire 1 is moved and/or rotated in a catheter, to securely prevent kinking (sharp bending) or torsion of the guide wire 1, especially kinking or torsion in the vicinity of weld portions.

Where a fluororesin (or a composite material thereof) is used, coating the wire body 10 with the resin can be conducted while keeping the resin material in a heated condition by a method such as baking and spraying. This promotes particularly excellent adhesion between the wire body 10 and the resin coating layers 8, 9.

In addition, where the resin coating layers 8, 9 are each composed of a silicone resin (or a composite material thereof), the resin coating layers 8, 9 in assured and firm adhesion to the wire body 10 can be formed, without need for heating at the time of forming the resin coating layers 8, 9 (at the time of coating the wire body 10). More specifically, where the resin coating layers 8, 9 are each composed of a silicone resin (or a composite material thereof), a reaction-curing type material or the like can be used, so that the formation of the resin coating layers 8, 9 can be carried out at room temperature. With the resin coating layers 8, 9 thus formed at room temperature, the coating can be carried out readily, and the guide wire 1 can be operated (steered) in the condition where a sufficient joint strength at the joint portions 17, 18 is maintained.

The resin coating layers 8, 9 (particularly the resin coating layer 8 on the distal side) can be also be provided for the purpose of enhancing safety while inserting the guide wire 1 into a blood vessel or the like. For this purpose, the resin coating layers 8, 9 are preferably composed of a material relatively rich in elasticity (soft material, elastic material).

Examples of materials relatively rich in flexibility include polyolefins such as polyethylene, polypropylene, etc., polyvinyl chloride, polyesters (PET, PBT, etc.), polyamides, polyimides, polyurethane, polystyrene, silicone resins, thermoplastic elastomers such as polyurethane elastomer, polyester elastomers, polyamide elastomers, etc., various rubber materials such as latex rubbers, silicone rubbers, etc., and composite materials obtained by combining two or more of these.

In the case where the resin coating layers 8, 9 are each composed of one of the above-mentioned thermoplastic elastomers and various rubber materials, the flexibility of the distal portion of the guide wire 1 is further enhanced. Thus, it is possible at the time of inserting the guide wire 1 into a blood vessel or the like, to securely prevent the guide wire 1 from damaging the blood vessel inside wall or the like, and to realize an extremely high safety.

The resin coating layers 8, 9 may each be a laminate of two or more layers. The resin coating layer 8 and the resin coating layer 9 may be composed of the same material or different materials. For example, the resin coating layer 8 located on the distal side of the guide wire 1 may be composed of the above-mentioned material rich in flexibility (soft material, elastic material), while the resin coating layer 9 located on the proximal side of the guide wire 1 may be composed of the above-mentioned material capable of reducing friction. This makes it possible to achieve simultaneous realization of both enhanced slidability (steerability) and enhanced safety.

The thicknesses of the resin coating layers 8, 9 are not particularly limited, and can be appropriately set in consideration of, for example, the purposes of forming the resin coating layers 8, 9, the materials constituting the resin coating layers 8, 9, the methods of forming the resin coating layers 8, 9. Typically, it is preferably for the resin coating layers 8, 9 to have a thickness of about 1 to 100 µm, more preferably about 1 to 30 µm. If the resin coating layers 8, 9 are too thin, the desired purpose for employing the resin coating layers 8, 9 may not be displayed sufficiently, and exfoliation of the resin coating layers 8, 9 may occur. On the other hand, if the resin coating layers 8, 9 are too thick, they may exert undesirable influences on the physical properties of the wire body 10, and exfoliation of the resin coating layers 8, 9 may be generated.

In the guide wire described here, the outer peripheral surface of the wire body 10 may be subjected to a treatment (a roughening treatment, a chemical treatment, a heat treatment, or the like) for enhancing adhesion of the resin coating layers 8, 9, or may be provided thereon with an intermediate layer which can enhance the adhesion of the resin coating layers 8, 9.

The outer surface of at least the distal portion of the guide wire 1 is preferably coated with a hydrophilic material. In this embodiment, the outer peripheral surface of the guide wire 1 in a region ranging from the distal end of the guide wire 1 to the vicinity of the proximal end of the intermediate member 5 is coated with a hydrophilic material. This helps ensure that the hydrophilic material exhibits lubricity upon being wetted, whereby friction (sliding resistance) of the guide wire 1 is reduced, and its slidability is enhanced. Accordingly, the steerability of the guide wire 1 is enhanced.

Examples of the hydrophilic material include cellulose based polymer materials, polyethylene oxide based polymer materials, maleic anhydride based polymer materials (for example, maleic acid copolymers such as methyl vinyl ether-maleic anhydride copolymer), acrylamide based polymer substances (for example, polyacrylamide, polyglycidyl methacrylate-dimethylacrylamide (PGMA-DMAA) block copolymer), water-soluble nylon, polyvinyl alcohol, and polyvinyl pyrrolidone.

These hydrophilic materials, in many cases, exhibit lubricity by being wetted (absorbing water) so as to reduce the frictional resistance (sliding resistance) between the guide wire 1 and the inside wall of a catheter used together with the guide wire 1. This enhances the slidability of the guide wire 1, leading to enhanced steerability of the guide wire 1 in a catheter.

As has been described above, according to the guide wire 1, the first wire 2 exhibiting quite good flexibility is provided on the distal side, while the second wire 3 exhibiting quite good rigidity characteristics is provided on the proximal side. This construction helps ensure that flexibility is sufficiently secured on the distal side of the guide wire 1, leading to relatively high safety, while sufficient rigidity is secured on the proximal side of the guide wire 1, leading to excellent pushability, torque transmission performance and traceability.

In addition, the first wire 2 and the second wire 3 can be connected to each other easily and firmly through the intermediate member 5.

Figure 2:
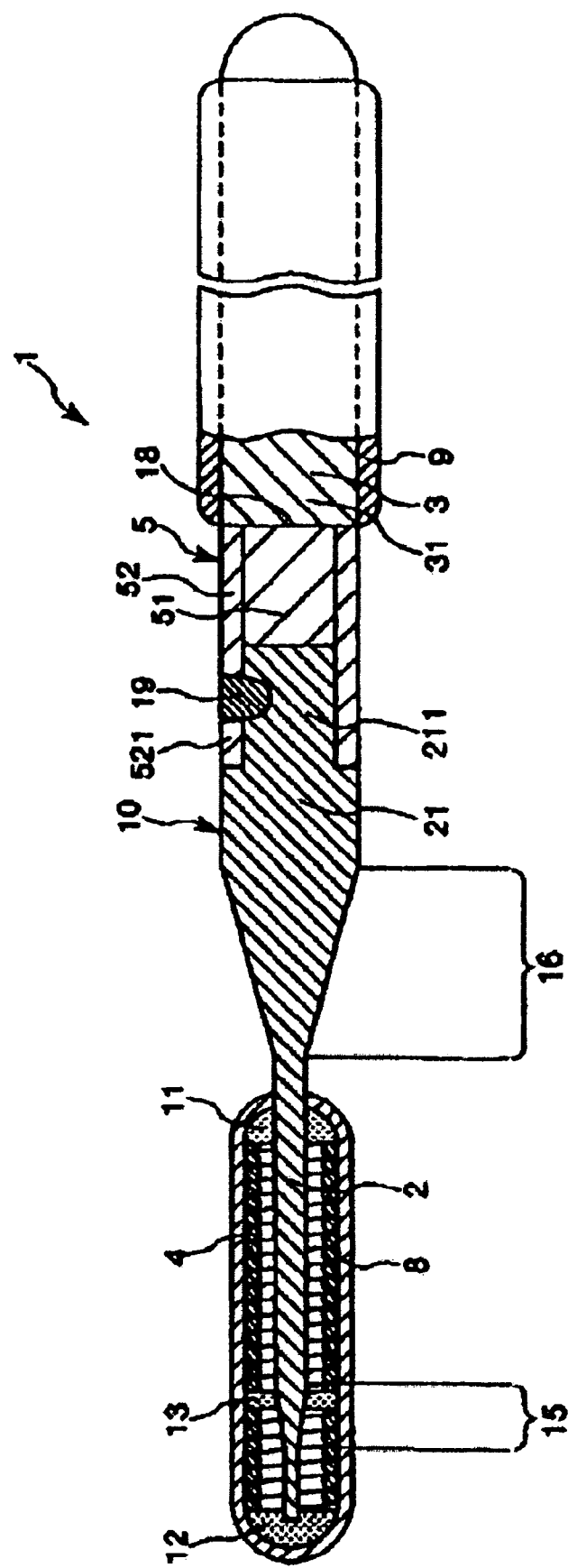
FIG. 2 is a longitudinal cross-sectional view of a second embodiment of the guide wire.

FIG. 2 illustrates, in longitudinal cross-section, a second embodiment of the guide wire. The description of this second embodiment of the guide wire 1 will focus primarily on differences relative to the first embodiment. Features in the second embodiment that are the same as those in the first embodiment are identified by the same reference numeral, and a detailed description of such features is not repeated.

The guide wire 1 in the second embodiment is the same as that in the first embodiment above, except for the configurations of the intermediate member 5 and the proximal portion 21 of the first wire 2.

As shown in FIG. 2, the guide wire 1 according to the second embodiment is configured such that the outer layer 52 of the intermediate member 5 includes an extension portion 521 extending in the distal direction beyond the distal end of the core portion 51. In addition, this extension portion 521 covers the outer periphery of the proximal portion 21 of the first wire 2.

Specifically, the proximal portion 21 of the first wire 2 has a smaller diameter portion (reduced diameter portion) 211 at the proximal end region of the first wire 2. The outer diameter of the smaller diameter portion 211 is smaller than the outer diameter of the adjoining larger diameter portion of the first wire 2, and the extension portion 521 covers the outer periphery of this small diameter portion 211. In the illustrated version shown in FIG. 2, the small diameter portion 211 and the extension portion 521 are dimensioned such that the outer surface of the extension portion 521 and the outer surface of the larger diameter portion of the proximal portion of the first wire 2 adjoining the small diameter portion 211 form a smooth continuation without any steps. Stated differently, the thickness of the extension portion 521 is equal to the difference in radius between the smaller diameter portion 211 of the first wire 2 and the adjoining larger diameter portion of the first wire 2. Additionally, the outer diameter of the core portion 51 of the intermediate member 5 is the same as the outer diameter of the smaller diameter portion 211.

The outer peripheral surface of the smaller diameter portion 211 (proximal portion 21) of the first wire 2 and the inner peripheral surface of the extension portion 521 (outer layer 52) of the intermediate member 5 are joined to each other, and the distal end face of the second wire 3 and the proximal end face of the intermediate member 5 are joined to each other. In this embodiment, a spot-formed weld portion 19 is formed as a joint portion between the small diameter portion 211 of the first wire 2 and the extension portion 521 of the intermediate member 5.

The core portion 51 is composed of the second material. In addition, the outer layer 52 is composed of the first material or a Ni alloy. Details associated with the Ni alloy are the same as in the first embodiment (Configuration 3).

In the case where the outer layer 52 is composed of the first material, the material constituting the first wire 2 and the material constituting the outer layer 52 are the same, the outer peripheral surface of the small diameter portion 211 (proximal portion 21) of the first wire 2 and the inner peripheral surface of the extension portion 521 (outer layer 52) are joined particularly firmly. In addition, since the material constituting the second wire 3 and the material constituting the core portion 51 are the same, the distal end face of the second wire 3 and the proximal end face of the core portion 51 are joined particularly firmly. As a result, the first wire 2 and the second wire 3 are firmly connected to each other through the intermediate member 5.

In the case where the outer layer 52 is composed of a Ni alloy, particularly where a Ni—Ti alloy is used as the first constituent material, the outer peripheral surface of the small diameter portion 211 (proximal portion 21) of the first wire 2 and the inner peripheral surface of the extension portion 521 (outer layer 52) are joined particularly firmly. In addition, since the material constituting the second wire 3 and the material constituting the core portion 51 are the same, the distal end face of the second wire 3 and the proximal end face of the core portion 51 are joined particularly firmly. As a result, the first wire 2 and the second wire 3 are firmly connected to each other through the intermediate member 5.

The proximal portion 21 of the first wire 2 is lower in rigidity than the part of the intermediate member 5 comprised of the core portion 51, and the distal end of the second wire 4 comprised of the small diameter portion 311 is higher in rigidity than the part of the intermediate member 5 comprised of the core portion 51.

The method for joining the proximal portion 21 of the first wire 2 and the extension portion 521 as the distal portion of the intermediate member 5 to each other and the method for joining the distal portion 31 of the second wire 3 and the proximal portion of the intermediate member 5 to each other are not particularly limited, and various methods can be used. The proximal portion 21 of the first wire 2 and the extension portion 521 of the intermediate member 5 are preferably joined to each other by welding, whereas the distal portion of the second wire 3 and the proximal portion of the intermediate member 5 are preferably joined to each other by welding, soldering or brazing.

The method for welding is not particularly limited. The welding of the proximal portion 21 of the first wire 2 and the extension portion 521 of the intermediate member 5 to each other is preferably laser welding. In addition, the welding of the distal portion 31 of the second wire 3 and the proximal portion of the intermediate member 5 to each other is particularly preferably butt resistance welding.

Figure 3:
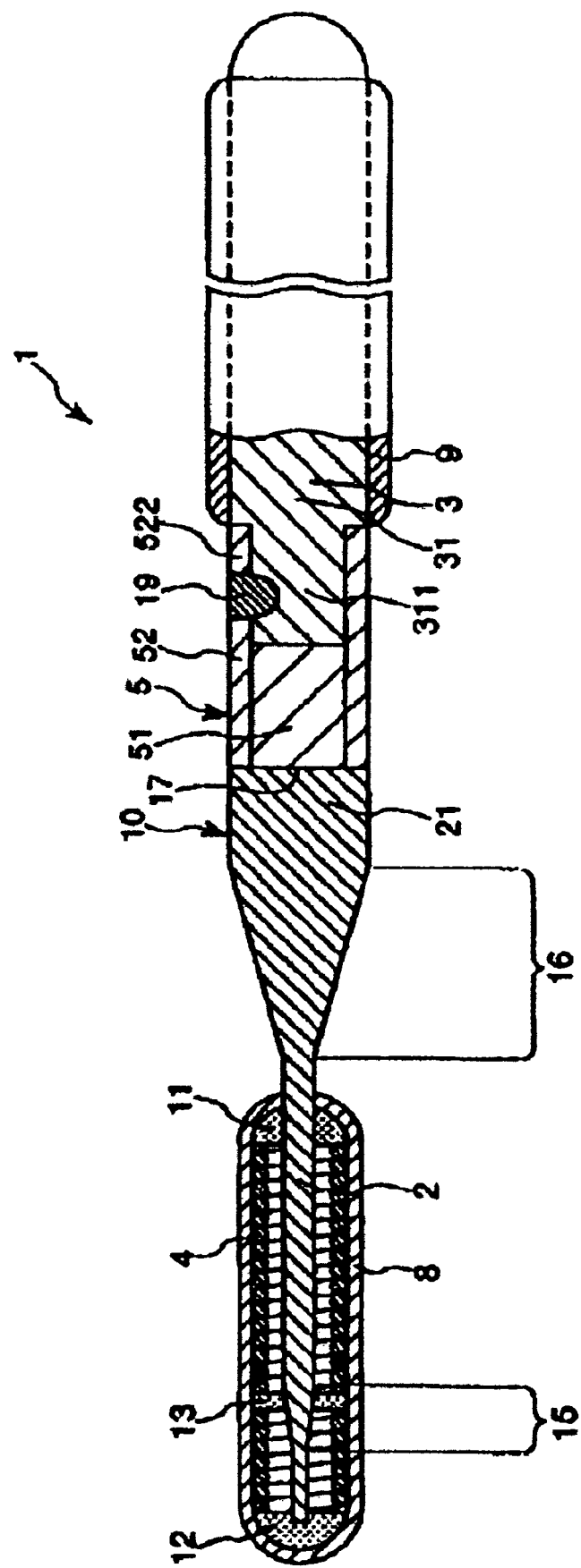
FIG. 3 is a longitudinal cross-sectional view of a third embodiment of the guide wire.

FIG. 3 illustrates, in longitudinal cross-section, a third embodiment of the guide wire. The description of this third embodiment of the guide wire 1 focuses primarily on differences relative to the first embodiment. Features in the third embodiment that are the same as those in the embodiments described above are identified by the same reference numeral, and a detailed description of such features is not repeated.

The guide wire 1 in the third embodiment is the same as that in the first embodiment described above, except for the configurations of the intermediate member 5 and the distal portion 31 of the second wire 3.

As shown in FIG. 3, in the guide wire 1 according to the third embodiment, an outer layer 52 of the intermediate member 5 has an extension portion 522 extended further toward the proximal side from the distal end of a core portion 51, and the extension portion 522 is covering the outer periphery of the distal portion 31 of the second wire 3.

Specifically, the distal portion 31 of the second wire 3 has a smaller diameter portion (reduced diameter portion) 311 whose outer diameter is reduced or contracted, and the extension portion 522 covers the outer periphery of the small diameter portion 311. In the illustrated version shown in FIG. 3, the smaller diameter portion 311 and the extension portion 522 are dimensioned such that the outer surface of the extension portion 522 and the outer surface of the larger diameter portion of the distal end portion 31 of the second wire 3 adjoining the small diameter portion 211 form a smooth continuation without any steps. Stated differently, the thickness of the extension portion 522 is equal to the difference in radius between the smaller diameter portion 311 of the second wire 3 and the adjoining larger diameter portion of the second wire 3. Additionally, the outer diameter of the core portion 51 of the intermediate member 5 is the same as the outer diameter of the smaller diameter portion 311.

The proximal end face of the first wire 2 and the distal end face of the intermediate member 5 are joined to each other, while the outer peripheral surface of the small diameter portion 311 (reduced diameter portion 31) of the second wire 3 and the inner peripheral surface of the extension portion 522 (outer layer 52) of the intermediate member 5 are joined to each other. In the configuration shown in the figure, a spot-formed weld portion 19 is formed as a joint portion between the small diameter portion 311 of the second wire 3 and the extension portion 522 of the intermediate member 5.

The core portion 51 is composed of the first material, while the outer layer 52 is composed of the second material.

This helps ensure that the material constituting the first wire 2 and the material constituting the core portion 51 are the same, so that the proximal end face of the first wire 2 and the distal end face of the core portion 51 are joined particularly firmly. In addition, since the material constituting the second wire 3 and the material constituting the outer layer 52 are the same, the outer peripheral surface of the smaller diameter portion 311 (distal portion 31) of the second wire 3 and the inner peripheral surface of the extension portion 522 (outer layer 52) are joined particularly firmly. As a result, the first wire 2 and the second wire 3 are firmly connected to each other through the intermediate member 5.

The proximal portion 21 of the first wire 2 is lower in rigidity than the part of the intermediate member 5 comprised of the core portion 51, and the part of the second wire 3 having the small diameter portion 311 is higher in rigidity than the part of the intermediate member 5 comprised of the core portion 51.

The method for joining the proximal portion 21 of the first wire 2 and the distal portion of the intermediate member 5 to each other, and the method for joining the distal portion 31 of the second wire 3 and the extension portion 522 as the proximal portion of the intermediate member 5 to each other are not particularly limited. Various methods can be used for this purpose, among which joining by welding is preferred.

The method of welding is not particularly limited. The welding of the proximal portion 21 of the first wire 2 and the distal portion of the intermediate member 5 to each other is particularly preferably butt resistance welding. In addition, the welding of the distal portion 31 of the second wire 3 and the extension portion 522 of the intermediate member 5 to each other is preferably laser welding.

Figure 4:
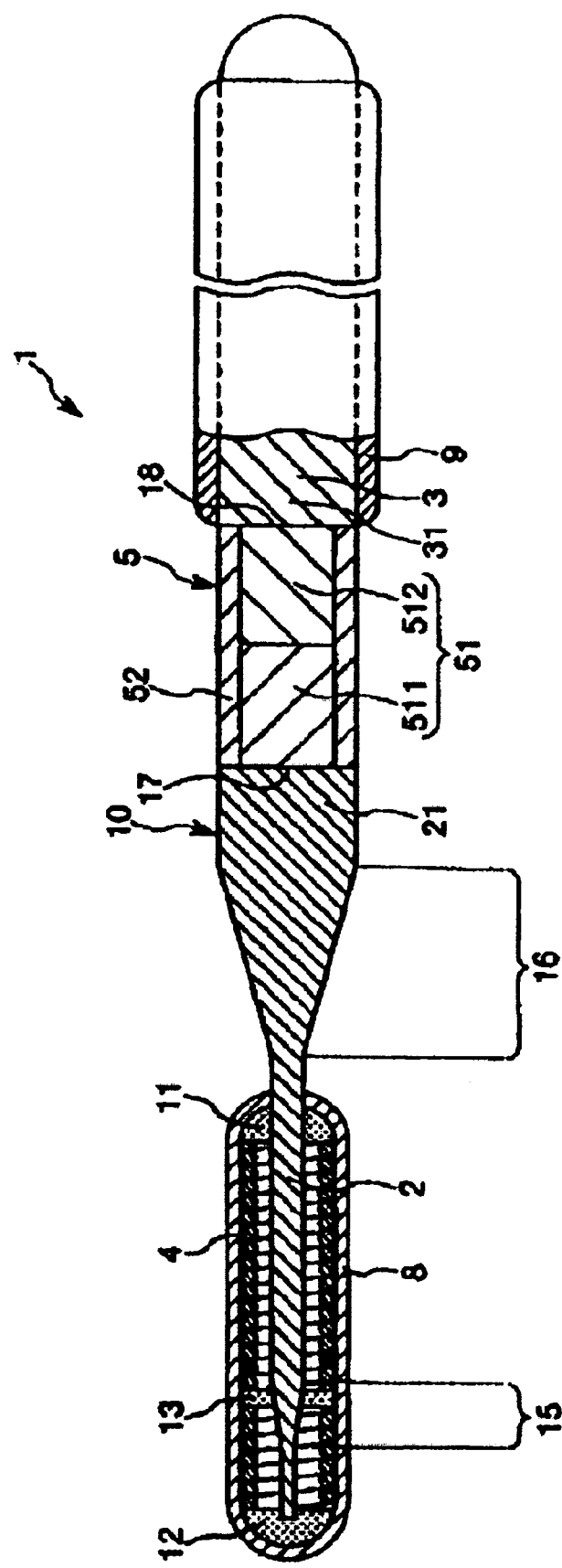
FIG. 4 is a longitudinal cross-sectional view of a fourth embodiment of the guide wire.

FIG. 4 illustrates, in longitudinal cross-section, a fourth embodiment of the guide wire. The description of this fourth embodiment of the guide wire 1 focuses primarily on differences relative to the first embodiment. Features in the fourth embodiment that are the same as those in the embodiments described above are identified by the same reference numeral, and a detailed description of such features is not repeated.

The guide wire 1 in the fourth embodiment is the same as that in the first embodiment above, except for the configuration of the intermediate member 5.

As shown in FIG. 4, the guide wire 1 according to the fourth embodiment includes an intermediate member 5 comprised of a core portion 51 and an outer layer 52. The core portion 51 of the intermediate member 5 is composed of a distal-side member 511 disposed on the distal side, and a proximal-side member 512 disposed on the proximal side of the distal-side member 511. The proximal-side member 512 is composed of a material different from the material of the distal-side member 511. In addition, a portion of the core portion 51, i.e., one of the distal-side member 511 and the proximal-side member 512, is composed of a material different from the material of the outer layer 52.

In the illustrated embodiment depicted in FIG. 4, the distal-side member 511 and the proximal-side member 512 are substantially cylindrical (columnar) in shape and possess the same outer diameter. In addition, the proximal end face of the distal-side member 511 and the distal end face of the proximal-side member 512 are in contact with (are facing) each other.

The distal-side member 511 is composed of the first material, and the proximal-side member 512 is composed of the second material.

As a result, the material constituting the first wire 2 and the material constituting the distal-side member 511 are the same, so that the proximal end face of the first wire 2 and the distal end face of the distal-side member 511 are joined particularly firmly. In addition, since the material constituting the second wire 3 and the material constituting the proximal-side member 512 are the same, the distal end face of the second wire 3 and the proximal end face of the proximal-side member 512 are joined particularly firmly.

The outer layer 52 is composed of the first material or the second material.

In the case where the outer layer 52 is composed of the first material, the material constituting the first wire 2 and the material constituting the outer layer 52 are the same, so that the proximal end face of the first wire 2 and the distal end face of the outer layer 52 are joined particularly firmly. In addition, in the case where the outer layer 52 is composed of the second material, the material constituting the second wire 3 and the material constituting the outer layer 52 are the same, so that the distal end face of the second wire 3 and the proximal end face of the outer layer 52 are joined particularly firmly.

As a result, the first wire 2 and the second wire 3 are firmly connected to each other through the intermediate member 5.

In the case where the outer layer 52 is composed of the first material, the proximal portion 21 of the first wire 2 is lower in rigidity than the part of the intermediate member 5 comprised of the proximal-side member 512, and the distal portion 31 of the second wire 3 is higher in rigidity than the part of the intermediate member 5 comprising the proximal-side member 512.

In the case where the outer layer 52 is composed of the second material, the proximal portion 21 of the first wire 2 is lower in rigidity than the part of the intermediate member 5 comprising the distal-side member 511, and the distal portion 31 of the second wire 3 is higher in rigidity than the part of the intermediate member 5 comprised of the distal-side member 511.

According to another embodiment, the guide wire 1 shown in FIG. 4 can be varied by utilizing a different material to fabricate the outer layer 52 of the intermediate member 5.

According to this fifth embodiment, the guide wire construction is the same as shown in FIG. 4, except that the outer layer 52 of the intermediate member 5 is composed of a Ni alloy containing Ni as a main constituent (composed mainly of Ni), i.e., a nickel-based alloy (an alloy in which the content, by weight, of Ni is the highest of the contents of elements constituting the alloy), or a Co alloy containing Co as a main constituent (composed mainly of Co), i.e., a cobalt-based alloy (an alloy in which the content, by weight, of Co is the highest of the contents of elements constituting the alloy).

The nickel-based alloy used to fabricate the outer layer 52 of the intermediate member 5 is not limited to any particular nickel-based alloy. By way of example, the nickel-based alloys described above in the first embodiment (Configuration 3) can be used.

In addition, the cobalt-based alloy to be used to fabricate the outer layer 52 is not particularly limited, but examples of the cobalt-based alloy include Co—Ni—Cr alloys, Co—Cr—Ni—Mo alloys, Co—Cr—W—Ni alloys, Co—Cr—Mo alloys, and Co—Ni—Cr—Mo—W—Fe alloys.

Preferable examples of the Co—Ni—Cr alloys include alloys containing 9 to 37 wt % of Ni, 10 to 30 wt % of Cr, and the balance of Co, or alloys obtained by replacing part of these alloys with other elements (substituent elements). Incidentally, where elements other than Co, Ni and Cr are contained in the alloy, the total content of them (all the substituent elements or elements other than Co, Ni and Cr) is preferably 30 wt % or below. In addition, part of Co, Ni, Cr may be replaced by other element(s).

With the outer layer 52 composed of a nickel-based alloy or a cobalt-based alloy, the proximal end face of the first wire 2 and the distal end face of the outer layer 52 are joined especially firmly, particularly in the case where a Ni—Ti alloy is used as the first constituent material. In addition, the distal end face of the second wire 3 and the proximal end face of the outer layer 52 are joined especially firmly, particularly in the case where a stainless steel is used as the second constituent material.

The proximal end face of the first wire 2 and the distal end face of the distal-side member 511 are joined particularly firmly, and the distal end face of the second wire 3 and the proximal end face of the proximal-side member 512 are joined particularly firmly. As a result of these configurations, the first wire 2 and the second wire 3 are firmly connected to each other through the intermediate member 5.

The method for joining the proximal portion 21 of the first wire 2 and the distal portion of the intermediate member 5 to each other, and the method for joining the distal portion 31 of the second wire 3 and the proximal portion of the intermediate member 5 to each other are not particularly limited, and various methods can be used for this purpose. The proximal portion 21 of the first wire 2 and the distal portion of the intermediate member 5 are preferably joined by welding, while the distal portion 31 of the second wire 3 and the proximal portion of the intermediate member 5 are preferably joined by welding or soldering (brazing).

Figure 5:
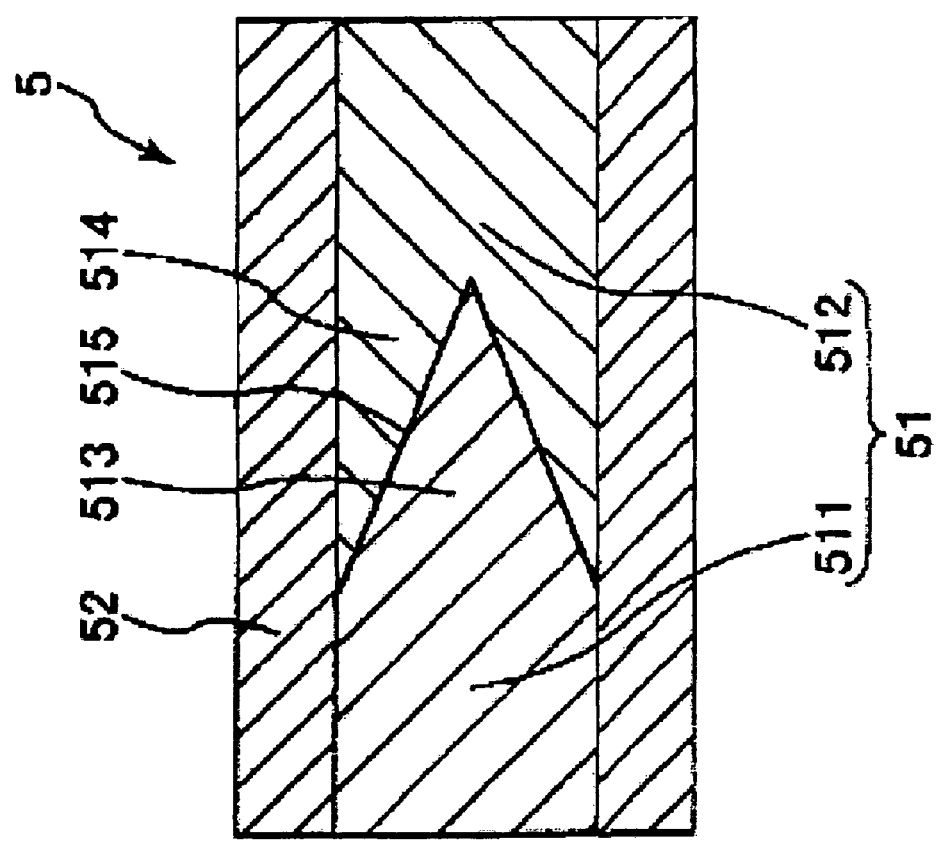
FIG. 5 is a longitudinal cross-sectional view of an intermediate member used in a further embodiment of the guide wire.

FIG. 5 illustrates, in longitudinal cross-section, a further embodiment of the guide wire. The description of this sixth embodiment of the guide wire focuses primarily on differences relative to the fourth embodiment. Features in this embodiment that are the same as those in the fourth embodiment described above are identified by the same reference numeral, and a detailed description of such features is not repeated.

The guide wire 1 in this sixth embodiment is the same as that in the fourth embodiment above, except for the shapes of the distal-side member 511 and the proximal-side member 512 of the core portion 51 of the intermediate member 5.

As shown in FIG. 5, in the guide wire 1 according to the sixth embodiment, the proximal portion 513 of the distal-side member 511 of the core portion 51 of the intermediate member 5 has a conical shape (inclusive of substantially conical shape) or a frustoconical shape (inclusive of substantially frustoconical shape). In the illustrated embodiment, the proximal portion 513 of the distal-side member 511 of the core portion 51 of the intermediate member 5 has a conical shape. The distal portion 514 of the proximal-side member 512 is provided with a recess 515 having a conical shape or a frustoconical shape corresponding to the shape of the proximal portion 513 of the distal-side member 511. In the illustrated embodiment, the recess 515 possesses a conical shape. The proximal portion 513 of the distal-side member 511 is inserted or positioned in the recess 515 in the proximal-side member 512.

This construction helps ensure that, in an intermediate portion or region of the intermediate member 5, the rigidity (flexural rigidity, torsional rigidity) of the wire body 10

(guide wire 1) is gradually reduced along the distal direction. As a result, kink resistance (resistance against sharp bonding) is enhanced, and the guide wire 1 possesses excellent steerability.

The rigidity of the intermediate member 5 is constant irrespective of the direction in which it is bent (irrespective of the radially outward direction), whereby excellent steerability can be secured.

The aspect of the sixth embodiment in which the proximal portion of a distal-side member is inserted or positioned in a recess in the distal portion of a proximal-side member is also applicable to the second, third and fifth embodiments described above. In applying this aspect to the second embodiment shown in FIG. 2, the proximal portion 21 (smaller diameter portion 211) of the first wire 2 would be appropriately configured to be received in a recess in the core portion 51. Similarly, in applying this aspect of the sixth embodiment to the third embodiment shown in FIG. 3, the distal portion 31 (smaller diameter portion 311) of the second wire 3 would be appropriately configured to include a recess that receives a similarly configured portion of the core portion 51.

In each of the embodiments of the guide wire described above, the outer diameter of the intermediate member 5 and the outer diameter of the first wire 2 are the same in a transition region (first transition region) at which the outer layer of the intermediate member 5 transitions to the first wire 2. Similarly, in each of the embodiments of the guide wire described above, the outer diameter of the intermediate member 5 and the outer diameter of the second wire 3 are the same in a transition region (second transition region) at which the outer layer of the intermediate member 5 transitions to the second wire 3. Thus, a smooth transition exists between the first wire and the outer layer of the intermediate member, and between the second wire and the outer layer of the intermediate member so that the outer surface of the guide wire in these regions presents a smooth outer surface without steps.

While the guide wire disclosed herein has been described above based on embodiments shown in the drawings, the guide wire of the present invention is not limited to the embodiments, and the configuration of component parts can be replaced by alternatives having the same or equivalent function. In addition, other components or features may be added.

In addition, in the present invention, configuration adapting two or more configurations (features) of the above-described embodiments can be applied.

In addition, the shape and position of the intermediate member 5 are not limited to those in the above-described embodiments. For example, the intermediate member 5 may be substantially frustoconical in shape. In the case where the intermediate member 5 is substantially frustoconical in shape, the intermediate member 5 is, for example, disposed at the tapered portion where the outer diameter of the wire body 10 is gradually reduced along the distal direction, i.e., at the gradually reduced outer diameter portion 16, so as to constitute part of the gradually reduced outer diameter portion 16. For example, the frustoconical intermediate member 5 may be located at the gradually reduced outer diameter portion 16. A taper angle of the frustoconical intermediate member preferably is the same as the angle of the gradually reduced outer diameter portion 16.

Also, the coil 4 may be omitted. In that case, a filler (particles) of a material having a contrast medium property (the above-mentioned radiopaque material or the like) is dispersed in the resin coating layer 8, thereby constituting a contrast portion.

The principles, preferred embodiment and other disclosed aspects of the guide wire have been described in the foregoing specification. However, the invention which is intended to be protected is not to be construed as limited to the particular embodiment and variations disclosed. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
   a first wire made of a first material;
   a second wire made of a second material different from the first material;
   the first wire being positioned at a distal portion of the guide wire;
   the second wire being positioned proximally of the first wire;
   an intermediate member positioned between the first wire and the second wire;
   the intermediate member comprising a core portion and an outer layer, the outer layer covering an outer periphery of the core portion;
   the core portion being at least in part made of a material different from material of which the outer layer is made;
   at least one of the core portion and the outer layer being made of the first material or the second material;
   the core portion possessing a distal end and a proximal end;
   the first wire possessing a proximal portion that is joined to a distal portion of the intermediate member;
   a portion of the first wire located distally of the proximal portion of the first wire possessing an outer diameter that decreases in a distal direction;
   the second wire possessing a distal portion that is joined to a proximal portion of the intermediate member;
   the outer diameter of the intermediate member and the outer diameter of the first wire being the same in a first transition region at which the outer layer of the intermediate member transitions to the first wire;
   the outer diameter of the intermediate member and the outer diameter of the second wire being the same in a second transition region at which the outer layer of the intermediate member transitions to the second wire;
   the core portion having a cylindrical shape and being a piece entirely separate from both the first wire and the second wire;
   the core portion and the outer layer are fixed to each other by crimping; and
   wherein i) a distal most end of the outer layer and a distal most end of the intermediate member lie in a common plane which is perpendicular to a longitudinal axis of the guide wire; or ii) a proximalmost end of the outer layer and a proximalmost end of the intermediate member lie in a common plane which is perpendicular to a longitudinal axis of the guide wire.

2. The guide wire as set forth in claim 1, wherein the proximal portion of the first wire is lower in rigidity than the intermediate member, and the distal portion of the second wire is higher in rigidity than the intermediate member.

3. The guide wire as set forth in claim 1, wherein the core portion is comprised of a distal-side member disposed on the distal side and a proximal-side member disposed on the proximal side of the distal-side member, the proximal-side member being formed of a material different from the material of which the distal-side member is formed, the proximal-side member having an outside diameter equal to the outside diameter of the distal-side member, and the outer layer extending from a distal end face of the distal-side member of the core portion to a proximal end face of the proximal-side member of the core portion.

4. The guide wire as set forth in claim 1, wherein the core portion possesses a distal end face and a proximal end face, and the outer layer of the intermediate member comprises an extension portion extending either distally beyond the distal end face of the core portion or proximally beyond the proximal end face of the core portion.

5. A guide wire comprising:
a wire body comprised of a first wire and a second wire;
the first wire being disposed on a distal side of the wire body and being comprised of a first material;
a second wire disposed on a proximal side of the first wire and comprised of a second material different from the first material;
an intermediate member positioned between the first and second wires, and connecting the first and second wires;
the intermediate member comprising a core portion and an outer layer covering an outer periphery of the core portion;
the core portion being composed in part or in whole of a material different from material of which the outer layer is composed, and at least one of the core portion and the outer layer being composed of the first material or the second material;
a proximal portion of the first wire and a distal portion of the intermediate member being joined to each other;
a distal portion of the second wire and a proximal portion of the intermediate member being joined to each other;
the core portion having a cylindrical shape and being a piece entirely separate from both the first wire and the second wire;
the core portion and the outer layer are fixed to each other by crimping; and
wherein i) a distal most end of the outer layer and a distal most end of the intermediate member lie in a common plane which is perpendicular to a longitudinal axis of the guide wire; or ii) a proximalmost end of the outer layer and a proximalmost end of the intermediate member lie in a common plane which is perpendicular to a longitudinal axis of the guide wire.

6. The guide wire as set forth in claim 5, wherein the first material is a Ni—Ti alloy.

7. The guide wire as set forth in claim 5, wherein the second material is a stainless steel.

8. The guide wire as set forth in claim 5, wherein the proximal portion of the first wire is lower in rigidity than the intermediate member.

9. The guide wire as set forth in claim 5, wherein the distal portion of the second wire is higher in rigidity than the intermediate member.

10. The guide wire as set forth in claim 5, wherein the wire body possesses an outside diameter that is constant along at least a portion of a longitudinal extent of the wire body ranging from a proximal portion of the first wire to a distal portion of the second wire.

11. The guide wire as set forth in claim 5, wherein the core portion is comprised of one of the first material and the second material, and the outer layer is comprised of an other of the first material and the second material.

12. The guide wire as set forth in claim 5, wherein the core portion is comprised of one of a Ni alloy and the second material, and the outer layer is comprised of an other of the Ni alloy and the second material.

13. The guide wire as set forth in claim 5, wherein the core portion is comprised of a distal-side member disposed on the distal side and a proximal-side member disposed on the proximal side of the distal-side member, the proximal-side member being formed of a material different from the material of which the distal-side member is formed.

14. The guide wire as set forth in claim 13, wherein the distal-side member is comprised of the first material, and the proximal-side member is composed of the second material.

15. The guide wire as set forth in claim 13, wherein the outer layer is comprised of the first material or the second material.

16. The guide wire as set forth in claim 13, wherein the outer layer is comprised of a Ni alloy or a Co alloy.

17. The guide wire as set forth in claim 13, wherein a proximal portion of the distal-side member possesses a tapering outer peripheral surface defining a tapering shape that narrows in a proximal direction, and a distal portion of the proximal-side member possesses a recess having a shape corresponding to the tapering shape of the proximal portion of the distal-side member, the proximal portion of the distal-side member being positioned in the recess.

18. The guide wire as set forth in claim 5, wherein a proximal end face of the first wire and a distal end face of the intermediate member are joined to each other, and a distal end face of the second wire and a proximal end face of the intermediate member are joined to each other.

19. The guide wire as set forth in claim 5, wherein the outer layer has an extension portion extending distally beyond a distal end of the core portion, and the extension portion covers an outer periphery of the proximal portion of the first wire.

20. The guide wire as set forth in claim 19, wherein the core portion is comprised of the second material.

21. The guide wire as set forth in claim 19, wherein the outer layer is comprised of the first material.

22. The guide wire as set forth in claim 19, wherein the outer layer is comprised of a Ni alloy.

23. The guide wire as set forth in claim 19, wherein an outer peripheral surface of the proximal portion of the first wire and an inner peripheral surface of the outer layer of the intermediate member are joined to each other, and a distal end face of the second wire and a proximal end face of the intermediate member are joined to each other.

24. The guide wire as set forth in claim 5, wherein the outer layer has an extension portion extending proximally beyond a proximal end of the core portion, and the extension portion covers an outer periphery of the distal portion of the second wire.

25. The guide wire as set forth in claim 5, wherein a proximal end face of the first wire and a distal end face of the intermediate member are joined to each other, and an outer peripheral surface of a distal portion of the second wire and an inner peripheral surface of the outer layer of the intermediate member are joined to each other.

26. A guide wire comprising:
a first wire made of a first material;
a second wire made of a second material different from the first material;
the first wire being positioned at a distal portion of the guide wire;
the second wire being positioned proximally of the first wire;

an intermediate member positioned between the first wire and the second wire;

the intermediate member comprising a core portion and an outer layer, the outer layer covering an outer periphery of the core portion;

the core portion being at least in part made of a material different from material of which the outer layer is made;

at least one of the core portion and the outer layer being made of the first material or the second material;

the core portion possessing a distal end and a proximal end;

the first wire possessing a proximal portion;

a portion of the first wire located distally of the proximal portion of the first wire possessing an outer diameter that decreases in a distal direction;

first means for joining a proximal end face of the first wire to a distal end face of the intermediate member;

second means for joining a distal end face of the second wire to a proximal end face of the intermediate member, the second means being distinct and spaced from the first means;

the outer diameter of the intermediate member and the outer diameter of the first wire being the same in a first transition region at which the outer layer of the intermediate member transitions to the first wire;

the outer diameter of the intermediate member and the outer diameter of the second wire being the same in a second transition region at which the outer layer of the intermediate member transitions to the second wire;

the core portion and the outer layer are fixed to each other by crimping; and wherein i) a distal most end of the outer layer and a distal most end of the intermediate member lie in a common plane which is perpendicular to a longitudinal axis of the guide wire; or ii) a proximalmost end of the outer layer and a proximalmost end of the intermediate member lie in a common plane which is perpendicular to a longitudinal axis of the guide wire.

\* \* \* \* \*